(12) United States Patent
Liu et al.

(10) Patent No.: US 6,781,018 B2
(45) Date of Patent: Aug. 24, 2004

(54) PROCESS AND CATALYST FOR PRODUCTION OF FORMALDEHYDE FROM DIMETHYL ETHER

(75) Inventors: Haichao Liu, Albany, CA (US); Enrique Iglesia, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/371,908

(22) Filed: Feb. 20, 2003

(65) Prior Publication Data

US 2004/0044252 A1 Mar. 4, 2004

Related U.S. Application Data

(63) Continuation-in-part of application No. 10/081,047, filed on Feb. 20, 2002, now abandoned.

(51) Int. Cl.[7] .............................................. C07C 45/37
(52) U.S. Cl. ...................... 568/470; 568/479; 568/485
(58) Field of Search ................................ 568/470, 479, 568/485

(56) References Cited

U.S. PATENT DOCUMENTS

| | | |
|---|---|---|
| 2,075,100 A | 9/1937 | Dreyfus |
| 2,246,569 A | 6/1941 | Brown |
| 2,487,223 A | 4/1949 | Payne |
| 3,655,771 A | 4/1972 | Tadenuma et al. |
| 4,435,602 A | 3/1984 | Lewis et al. |
| 4,439,624 A | 3/1984 | Lewis et al. |
| 4,442,307 A | 4/1984 | Lewis et al. |
| 6,265,528 B1 | 7/2001 | Hagen et al. |

OTHER PUBLICATIONS

Centi, G., "Nature of active layer in venedium oxide supported on titanium oxide and control of its reactivity in the selective oxidation and ammoxidation of alkylaromatics," Applied Catalysis, 1996, pp. 267–298, vol. 147.

Chen, K. et al., "Alkali effects on molybdenum oxide catalysts for the oxidative dehydrogenation of propane," Journal of Catalysis, 2000, pp. 244–252, vol. 195.

Chen, K. et al., "Catalytic properties of supported $MoO_3$ catalysts for oxidative dehydrogenation of propane," *Studies in Surface Science and Catalysis*, Spivey, J.J. et al., eds. 2001.

Chen, K. et al., "Isotopic tracer studies of reaction pathways for propane oxidative dehydrogenation on molybdenum oxide catalysis," J. Phys. Chem. B., 2001, pp. 648–653, vol. 105.

Chen, K. et al., "Kinetics and mechanism of oxidative dehydrogenation of propane on vanadium, molybdenum, and lungsten oxides," J. Phys. Chem. B., 2000, pp. 1292–1299, vol. 104.

Chen, K. et al., "Structure and properties of oxidative dehydrogenation catalysis based on $MoO_3/Al_2O_3$," Journal of Catalysis, 2001, pp.232–242, vol. 198.

Chen, K. et al., "Stucture and properties of zirconia–supported molybdenum oxide catalysis for oxidative dehydrogenation of propane," Journal of Catalysts, 2000, pp. 421–430, vol. 169.

Deo, G. and Wachs, I.E., "Reactivity of supported vanadium oxide catalysis: The partial oxidation of methanol," Journal of Catalysts, 1994, pp. 323–334, vol. 146.

Fleisch, T.H. et al., "Dimethyl ether: A fuel for the $21^{st}$ century," Studies in Surface Science and Catalysis, 1997, pp. 117–125, vol. 107.

Hara, M. et al., "Thermal conversion of methoxy species on dimethyl ether adsorbed $CeO_2$, " J. Phys. Chem., 1996, pp. 14462–14467, vol. 100.

Jehng, J.M., "Dynamic states of $V_2O_5$ supported on $SnO_2/SiO_2$ and $CeO_2/SiO_2$ mixed–oxide catalysts during methanol oxidation," J. Phys. Chem. B., 1998, pp. 5816–5822, vol. 102.

Khodakov, A. et al., "Structure and properties of vanadium oxide–zirconia catalysts for propane oxidative dehydrogenation," Journal of Catalysis, 1998, pp. 343–351, vol. 177.

Khodakov, A., "Structure and catalytic properties of supported vanedium oxides: Support effects on oxidative dehydrogenation reactions," Journal of Catalysis, 1999, pp. 205–216, vol. 181.

Liu, Z. and Chen, Y., "Spectroscopic studies on tetragonal $ZrO_2$–supported $MoO_3$ and $NiO$–$MoO_3$ systems," Journal of Catalysis, 1998, 314–324, vol. 177.

Olthof, B. et al., "Effects of Support composition and pretreatment conditions on the structure of vanadia dispersed on $SiO_2$ $Al_2O_3$, $TiO_2$, $ZrO_2$, and $HfO_2$, " J. Phys. Chem. B, 2000, pp. 1516–1528, vol. 104.

Ouyang, F. and YAO, S., "Infrared study of $ZrO_2$ surface sites using adsorbed probe molecules. 2. Dimethyl either adsorption," J. Phys. Chem. B., 2000, pp. 11253–11257, vol. 104.

Tatibouet, J.M., "Methanol oxidation as a catalytic surface probe," Applied Catalysis A., 1997, pp. 213, 252, vol. 148.

Xie, Y.C. and Tang, Y.Q., "Spontaneous monolayer dispersion of oxide and salts onto surfaces of supports: Applications to heterogeneous catalysis," Advances in Catalysis, 1990, pp. 1–42, vol. 37.

*Primary Examiner*—Samuel Barts
*Assistant Examiner*—Sikarl A. Witherspoon
(74) *Attorney, Agent, or Firm*—Townsend and Townsend and Crew LLP

(57) ABSTRACT

Dimethyl ether is converted to formaldehyde using a supported catalyst comprising molybdenum and/or vanadium oxides. The surface density of the oxide(s) ranges from greater than that for the isolated monomeric oxides upwards, so long as there is a substantial absence of bulk crystalline molybdenum and/or vanadium oxide(s). Conversion and selectivity to formaldehyde are improved as compared to data reported for known catalysts. Also disclosed is a supported catalyst comprising molybdenum and/or vanadium oxides wherein the support comprises one or more reducible metal oxides, preferably a layer or layers of one or more reducible metal oxides disposed on the surface of a particulate alumina or zirconia support.

62 Claims, No Drawings

PROCESS AND CATALYST FOR PRODUCTION OF FORMALDEHYDE FROM DIMETHYL ETHER

CROSS-REFERENCE TO RELATED APPLICATIONS

This is a continuation-in-part of application Ser. No. 10/081,047 filed Feb. 20, 2002 now abandoned.

FIELD AND BACKGROUND OF THE INVENTION

This invention relates to a process for production of formaldehyde, and optionally also methyl formate as a co-product, by oxidation of dimethyl ether (DME), and to catalysts for use in the process, including catalysts that are novel per se. In addition, this invention relates to the use of such novel catalysts in other processes.

Formaldehyde is widely used as an intermediate or basic building block in the commercial synthesis of many chemicals. Because of the existence of large reserves of methane worldwide it has been considered desirable for some time to develop processes to convert methane to more valuable chemicals. One such effort has been in the area of direct conversion of methane to formaldehyde via selective oxidation. However, this has not been particularly successful. Up to now, all such processes have resulted in low yields due to the tendency of the formaldehyde so produced being further oxidized to carbon oxides under the severe reaction conditions required for methane oxidation.

Instead, formaldehyde is commercially produced from methane indirectly, for instance, by first converting the methane to synthesis gas (CO and $H_2$), then reacting that to form methanol, and finally oxidizing the methanol to produce formaldehyde. The oxidation of methanol to formaldehyde has been extensively studied, and is the dominant process today for formaldehyde synthesis, typically using silver- or iron/molybdenum-based catalysts.

Another possible route to formaldehyde involves the oxidation of dimethyl ether ($CH_3OCH_3$) via cleavage of the C—O—C linkages. This process, however, has not been widely studied.

Dimethyl ether is a generally environmentally benign molecule. Its physical properties resemble those of LPG (liquefied petroleum gases), and dimethyl ether thus can be transported within existing and developing LPG infrastructures. Like methanol, dimethyl ether can be produced from synthesis gas. These characteristics give it the potential to be a new, clean alternative fuel. This potential is expected to lead to the production of substantially larger quantities of dimethyl ether than in the past, thus making it available for use as an intermediate in production of other chemicals, including formaldehyde.

Several patents disclose processes for producing formaldehyde from dimethyl ether using various catalysts. U.S. Pat. No. 2,075,100 describes such a process using a number of comparatively mild oxidation catalysts including platinum wire or foil, palladium black, and metals such as gold, silver, and copper. Vanadium pentoxide and iron, chromium and uranium sesqui-oxides are termed "very suitable". U.S. Pat. No. 3,655,771 describes using catalysts containing tungsten oxide, alone or optionally with no more than 10% of an additive. The additives mentioned include bismuth, selenium, molybdenum, vanadium, phosphorus and boron oxides, as well as phosphoric acid, ammonium phosphate and ammonium chloride.

More recently, U.S. Pat. No. 4,435,602 describes a process for production of formaldehyde from dimethyl ether using naturally occurring manganese nodules as a catalyst. U.S. Pat. No. 4,439,624 describes such a process using an intimate mixture of bismuth, molybdenum and copper oxides, preferably prepared by coprecipitation. U.S. Pat. No. 4,442,307 describes such a process using an intimate mixture of bismuth, molybdenum and iron oxides, similarly prepared. U.S. Pat. No. 6,256,528 describes oxidation of dimethyl ether with a catalyst containing metallic silver to produce a mixture of products including formaldehyde, light alkanes, carbon oxides and water. Information in these patents indicates that formaldehyde was produced with reasonable yields, but that overoxidation of that product to carbon oxides occurred to an undesirable degree.

As described above, it would be advantageous to provide a process and associated process technology for production of formaldehyde from dimethyl ether with good conversion and good selectivity to formaldehyde. Preferably such a process could be operated without the occurrence of substantial direct oxidation of dimethyl ether to carbon oxides or further oxidation of product formaldehyde to carbon oxides, thus improving the chemical and energy efficiency of the process.

BRIEF SUMMARY OF THE INVENTION

In brief, in one aspect, this invention comprises a process for the production of formaldehyde by oxidation of dimethyl ether in the presence of a supported catalyst comprising molybdenum oxide, vanadium oxide or a mixture of molybdenum and vanadium oxides. The support is one that substantially does not react with the molybdenum or vanadium oxide to form unreducible mixed oxide(s). Preferred supports comprise alumina, zirconia, stannic oxide, titania, silica, ferric oxide, ceric oxide, other reducible metal oxides, and mixtures and combinations thereof.

In one preferred embodiment this invention comprises such a process in which the molybdenum and/or vanadium oxides are dispersed on the surface of the support, the surface density of the oxide or oxides on the support is greater than that for the isolated monomeric oxide or oxides, and in which the catalyst is characterized by a substantial absence of bulk crystalline molybdenum and/or vanadium oxides.

Most preferably the surface density of the molybdenum and/or vanadium oxide or oxides on the support is approximately that of a monolayer of the oxide or oxides at the surface of the support.

In another preferred embodiment, the catalyst comprises one or more reducible metal oxides. More preferably in this embodiment, the catalyst comprises a layer of the reducible metal oxide or oxides, most preferably stannic oxide, on a particulate support (preferably alumina and/or zirconia) with the molybdenum and/or vanadium oxide or oxides being present as an upper layer or layers on the layer of reducible metal oxide(s) layer. In this embodiment, preferably the surface density of the molybdenum and/or vanadium oxide or oxides on the support is greater than that for the isolated monomeric oxide or oxides, and the catalyst is characterized by a substantial absence of bulk crystalline molybdenum and/or vanadium oxides. Most preferably the surface density of the molybdenum and/or vanadium oxide or oxides on the support is approximately that of a monolayer of the oxide or oxides at the surface of the support.

Catalysts of the above type in which the catalyst comprises one or more reducible metal oxides, particularly stannic oxide, and more particularly in which the molybdenum and/or vanadium oxide is supported on a layer or layers of reducible metal oxide or oxides, with the oxide layer or layers being disposed on a particulate alumina and/or zirconia, are novel and form another feature of this invention.

Yet another aspect of this invention is the use of the novel catalysts just described to catalyze other processes, particularly oxidation of methanol to formaldehyde, oxidative dehydrogenation of alkanes, and oxidation of alkenes.

DETAILED DESCRIPTION OF THE INVENTION

In brief, a primary aspect of this invention comprises a process for the production of formaldehyde by oxidation of dimethyl ether in the presence of a supported catalyst comprising molybdenum oxide, vanadium oxide or a mixture of molybdenum and vanadium oxides. Preferably the oxides are supported on alumina ($Al_2O_3$) and/or zirconia ($ZrO_2$), and more preferably on such a support that also includes one or more reducible metal oxides, as described herein. Preferably, the molybdenum and/or vanadium oxides are dispersed on the surface of the support, the surface density of the oxide or oxides on the support is greater than that for the isolated monomeric oxide or oxides, and the catalyst is characterized by a substantial absence of bulk crystalline molybdenum or vanadium oxides. More preferably the molybdenum and//or vanadium oxides are dispersed on a layer or layers of a reducible oxide or oxides that is further supported on alumina, titania, silica or zirconia (if zirconia is not used as the above-mentioned layer).

Catalysts of this type that comprise molybdenum or vanadium oxides supported on alumina or zirconia are described in several prior publications, for catalyzing the oxidative dehydrogenation of propane to propene. These include Chen, et al., in "Studies in Surface Science and Catalysis", Vol. 136, pp. 507–512, J. J. Spivey, E. Iglesia and T. M. Fleisch, Ed. (Elsevier Science, B.V., 2001); Chen et al., J. Catalysis 189, 421 (2000), Khodakov et al., J. Catalysis 177, 343 (1998), Chen et al., J. Catalysis 198, 232 (2001) and Chen et al., J. Phys. Chem. B2011, 105, 646 (2001). These publications are hereby incorporated herein by reference. However, these publications do not disclose catalysts containing stannic oxide, titania, silica, or other supports, and do not discuss the usefulness or potential usefulness of the disclosed catalysts for reactions such as the production of formaldehyde from dimethyl ether.

In the catalysts of this invention, the molybdenum and/or vanadium oxide is distributed on the surface of the support material in what is known as "small domain" distribution. The surface density of the oxide catalyst on the support (measured in units of Mo or V metal atoms per $nm^2$) is chosen so as to be greater than the surface density of the respective isolated monomeric oxide or oxides, but the catalyst overall is characterized by a substantial absence of bulk crystalline molybdenum and/or vanadium oxides (corresponding to the oxide or oxides used in preparing the catalyst). By "bulk crystalline oxides" is meant oxide(s) having a clear X-ray diffraction pattern. The crystallinity can be determined by X-ray diffraction based on the peak intensity ratio between one of the peaks of the supported metal oxide and one of the peaks of the support employed after calibration with a mixture of known amounts of the metal oxide and the support. By "substantial absence" is meant that the supported catalyst contains less than about 5% of bulk crystalline molybdenum and/or vanadium oxide(s).

Surface densities of the catalysts in this invention are given in terms of nominal surface density. This value is calculated based on the elemental analysis of the molybdenum and/or vanadium oxide and on the surface area of the support, i.e., by dividing the number of metal atoms of the catalytic metal (Mo or V) in a given mass of sample by the surface area of the support (calculated from $N_2$ absorption at its normal boiling point using the Brunauer-Emmett-Teller, or BET, equation). Where the metal oxide does not appreciably interact with the support to form a complex (as described below), this calculated surface density fairly closely conforms to the actual surface density of the metal atoms on the surface of the support. However, where an appreciable amount of a complex is formed between the metal oxide and the support, the (nominal) surface density represents what that value would be were a complex not formed.

The surface density of the catalyst affects the catalyst efficiency. At one extreme, catalysts of this type with relatively isolated oxide species, for example monomolybdate or monovanadate species, have relatively few active sites on the support surface. These catalysts tend to retain their oxygen and thus provide rather low reaction rates for the oxidation of dimethyl ether to formaldehyde. At the other extreme, catalysts having bulk crystals may possibly provide reasonable reaction rates per unit surface area. However, they also lack efficiency in the utilization of the oxide catalyst because a substantial amount of the oxide is located within the crystals and is thus not available for catalyzing the reaction. Bulk $MoO_3$ crystals also tend to be nonselective in their functioning, and can cause overreaction to produce carbon oxides rather than the desired products formaldehyde and methyl formate.

It has been found that the most preferred catalysts for this reaction tend to have a surface density of approximately a monolayer of catalyst on the support. The monolayer surface density depends primarily on the oxide chosen. For molybdenum oxide, the monolayer surface density is ~5.0 Mo atoms per square nanometer of support (Xie et al, Adv. Catal., 37, 1 (1990)). For vanadium oxide, this value is approximately 7.5 V atoms per square nanometer (Centi, Appl. Catal. A, 147, 267 (1996)). The term "monolayer" as used herein is meant to refer to these approximate surface densities. If the catalyst is uniformly dispersed on the support, satisfactory results are obtainable with a preferred surface density of from approximately 50–300% of the monolayer capacity values for alumina supports, and approximately 50–400% of these values for zirconia supports. Overall, a preferred range of surface densities is from about 50 to about 300% of the monolayer capacity, for both molybdenum and vanadium oxides, for all supports usable in this invention.

The molybdenum or vanadium oxide may be present as the oxide per se, represented by the general formulas $MoO_x$ and $VO_y$, where x and y represent general values for oxygen in such molecules. For $MoO_x$, the oxide generally comprises about three oxygen atoms per molybdenum atom; i.e., the general form of the oxide may be represented as $MoO_3$, or molybdenum trioxide. For $VO_y$, the oxide generally comprises about five oxygen atoms per two vanadium atoms, represented by the general formula $V_2O_5$, or vanadium pentoxide. However, in a given case the oxide may have an oxygen-to-metal atomic ratio that is not necessarily exactly 3:1 for molybdenum oxides or 5:2 for vanadium oxides. Likewise, oxides used as a component of the support may be represented by more general formulas such as $SnO_x$, $FeO_x$ and $CeO_x$, where the oxides generally comprise about 2, 1.5 and 2 oxygen atoms per metallic atom, respectively. However, in a given case, such oxide may have an oxygen-to-metal atomic ratio that is not exactly these values.

In addition, the molybdenum or vanadium oxides may form one or more complexes or compounds with the support. These complexes usually also will be an oxide such as polymolybdates and/or polyvanadates. Such molybdenum complexes may have general formulas such as $ZrMo_2O_8$. Vanadium complexes would generally be represented by the formula $M_{2x}V_{2y}O_{(nx+5y)}$ where M is the cationic ion of the support and n is the oxidation state of M, e.g., $ZrV_2O_7$. In any case, such complexes of molybdenum and vanadium oxides with the support are considered to be within the definition of the oxide catalysts to which this invention pertains.

For instance, with molybdenum oxide supported on zirconia, as seen in examples below, where the Mo surface density is below 6.4 Mo/nm$^2$ the $ZrO_2$ surface is covered predominantly by two-dimensional polymolybdates (irrespective of the temperature of preparation), and the $MoO_x$ domain size increases with increasing the Mo surface density. At Mo surface densities above 6.4 Mo/nm$^2$, increase in the Mo surface density leads to the preferential formation of $MoO_3$ or $ZrMo_2O_8$ crystallites on the $ZrO_2$ surface after treatment in air at 723 and 773 K or at 873 K, respectively. This makes a fraction of the Mo active centers inaccessible to dimethyl ether reactions and thus, as described below, leads to a monotonic decrease in the primary dimethyl ether reaction rates with increasing Mo surface density (>6.4 Mo/nm$^2$).

For such samples where the surface density was greater than 6.4 Mo/nm$^2$, the areal dimethyl ether reaction rates (per surface area) and primary selectivities approached constant values as the Mo surface density increased. This indicates that the $MoO_3$ or $ZrMo_2O_8$ domains at the $ZrO_2$ surface do not change in their local structure or surface properties, while their domain size grows with increasing the Mo surface density. The surface density of 6.4 Mo/nm$^2$ exceeds the theoretical polymolybdate monolayer, which is about 5.0 Mo/nm$^2$. Nevertheless, the catalyst sample with a surface density of 6.4 Mo/nm$^2$ exhibited the highest dimethyl ether reaction rates among the zirconia-supported molybdenum catalyst samples. This appears to be a compromise between reactivity and accessibility of the $MoO_x$ sites. The samples having a $ZrMo_2O_8$ structure possess a higher reactivity compared to the samples having polymolybdates and $MoO_3$ crystallines at a given Mo surface density, which is believed to be a result of the higher reducibility of the $ZrMo_2O_8$ species. The reducibility of the $MoO_x$ domains (characterized by a $H_2$ temperature-programmed reduction method) was found also to be dependent on the domain size and structures of the $MoO_x$ species. The larger $MoO_x$ domains undergo faster reduction compared to the smaller ones, and $ZrMo_2O_8$ domains are more reducible than two-dimensional polymolybdate and $MoO_3$ domains at a given Mo surface density, reflecting the difference in the ability of these species to delocalize charge.

The support may be selected among commonly used supports for such oxide catalysts, including mixtures of such supports, provided it allows or favors the formation of a monolayer of molybdenum and/or vanadium oxide on the surface of the support and otherwise is suitable for use in the production of formaldehyde from dimethyl ether. Some properties may make certain supports unsuitable for use in the process of this invention. For instance, supports that will react with the molybdenum and/or vanadium oxide to form any significant amounts of unreducible mixed bulk oxides, i.e. oxides that would undergo substantial formation of oxygen vacancies at temperatures below about 300–400° C., would in general not be suitable for use in this process. One commonly used catalyst support, magnesium oxide, for example, was tested for suitability in this process and was found unsuitable. Supports that could cause undesired combustion of products to form carbon oxides under the operating conditions of this process, or that contain acid sites that could cause formation of excessive amounts of methanol under the conditions of this process also would not be suitable for use in this invention.

The catalyst preferably contains molybdenum or vanadium oxide, but may contain a combination of the two. When both oxides are present in the catalyst, one may be present as a layer of oxide on the support, preferably close to a monolayer, and the other present as a layer on top of the first oxide layer. Catalysts of this invention thus may comprise a layer, preferably approximately a monolayer, of one of molybdenum or vanadium oxide on a layer, preferably approximately a monolayer, of the other, on a support such as alumina or zirconia. The support may optionally further comprise a reducible metal oxide as described below.

Preferred supports include alumina, zirconia, titania, silica, and reducible metal oxides such as stannic oxide, ferric oxide, ceric oxide, and mixtures or other combinations of two or more of these oxides. Particularly preferred are alumina, zirconia and stannic oxide, and mixtures or other combinations of two or all three of them. Most preferred is a catalyst comprising alumina, titania, zirconia or silica modified by the incorporation of a layer or layers of a reducible oxide such as zirconia, stannic oxide, ferric oxide or ceric oxide deposited thereon. The supports that are suitable for use in this process may be used in any of their available forms, including forms that as of the present time might not yet have been developed, or may have been developed but have not yet been commercialized. Both high and low surface area supports may be used, including materials known by the acronym MCM (standing for Mobil Compositions of Matter), e.g., MCM-41. These are recently developed mesoporous materials (often comprising silica) and are described in Kresge, et al., (Nature, 359, 710 (1992)) and by Corma (Chem. Rev., 97, 2373 (1997)). High surface area supports of various physical types are preferred for use in the invention from the point of view of efficiency in that they may produce greater amounts of product per unit mass of overall catalyst.

Reducible metal oxides suitable for inclusion in the catalysts of this invention are those in which at least a fraction of the metal cations undergo a one- or two-electron reduction during contact with a reactant such as hydrogen, dimethyl ether, methanol, alkanes or alkenes at typical temperatures of catalytic oxidation reactions, whether or not such metal oxides function as catalyst for the reaction in question. The fraction of the reducible metal oxide that undergoes such reduction need not be large, as the effect of the reducible metal oxide is continuous. Such reducible metal oxides include reducible oxides of tin, iron, cerium, manganese, cobalt, nickel, chromium, rhenium, titanium, silver and copper, and mixtures thereof. Of these, oxides of tin (e.g., stannic oxide), iron (e.g., ferric oxide) and cerium (e.g., ceric oxide) are preferred, with stannic oxide being most preferred for such catalysts of this invention.

Novel catalysts of this invention include those in which the support comprises a layer of a reducible metal oxide disposed on a particulate alumina and/or zirconia (except where zirconia is used as the above-mentioned layer), or a layer of zirconia disposed on a particulate alumina, particularly those in which the layer of or zirconia has a surface density close to that of a monolayer of that substance. Exemplary catalysts may comprise molybdenum and/or vanadium oxide on a near-monolayer of stannic oxide disposed on a particulate (preferably high surface area) alumina. Novel catalysts of this invention also include those in which the reducible metal oxide or oxides is incorporated into the support.

Without intending to be bound by an explanation, it is believer that the reducible metal oxides aid in catalyst performance by decreasing the temperature required for the reduction of some of the molybdenum and/or vanadium atoms from their highest oxidation state.

The novel catalysts of this invention that contain reducible metal oxides also are suitable as catalysts for other reactions and processes, including but not limited to oxidation of methanol to produce formaldehyde, oxidative dehydrogenation of alkanes, and oxidation of alkenes.

The catalysts of the invention are prepared by typical means, for instance by impregnation, particularly incipient wetness impregnation, of the support with an aqueous solution containing molybdenum and/or vanadium, e.g. using a salt such as an ammonium molybdate or vanadate, for instance, ammonium di- or heptamolybdate or ammonium metavanadate. The preparation is carried out so as to disperse the molybdenum and/or vanadium oxide over the surface of the support and the amounts are chosen so as to achieve a desired surface density. Where the catalyst also comprises a reducible metal oxide, for instance as a layer on a particulate support, the reducible metal oxide may be first deposited on the particulate support, for instance by impregnation such as incipient wetness impregnation. Then the molybdenum and/or vanadium oxide is deposited on the support in a second step, e.g. a second impregnation. Preparation of such catalysts by incipient wetness impregnation is described in the Chen et al. and Khodakov et al. publications mentioned above.

Catalysts of this invention may alternatively be prepared by other means such as chemical vapor deposition of layers, precipitation, sol-gel methods and the like. Reducible metal oxides may be incorporated into the catalysts either before or after the incorporation of the molybdenum and/or vanadium oxides.

The primary products of the reaction are formaldehyde and methyl formate. Production of methyl formate can be increased if desired, by decreasing the surface density of metal oxide or choosing a specific support such as stannic oxide and/or zirconia, or it may be decreased (which is generally preferred since formaldehyde is typically the preferred product) by providing a catalyst having a surface density close to the value for a monolayer of catalyst, which, as will be shown below, generally has the highest selectivity to formaldehyde of the catalysts of the invention. However, production of methyl formate is to be expected in such a process, and is not especially detrimental as methyl formate has uses of its own as a chemical intermediate and can readily be separated from the reaction products and forwarded to other process units for such uses.

Methanol is also produced in processes of this type, but it dehydrates relatively readily to re-form dimethyl ether. The methanol produced can be recovered and recycled. Alternatively, methanol produced by this reaction may be forwarded to another unit, either for production of further formaldehyde using a typical catalyst for that process, or for other uses as a chemical intermediate. Methanol formation therefore can be essentially disregarded in calculating selectivity of the dimethyl ether to formaldehyde.

The feed to the process may include, in addition to dimethyl ether, mixtures of dimethyl ether and methanol, provided that dimethyl ether is the major component of such mixtures. The oxidizing agent may be air, oxygen-enriched air, or even pure oxygen (though this is likely to be unnecessarily costly).

The process of this invention may be run in equipment ranging in size from microreactors (e.g. microchannel reactors) to full-sized commercial process equipment. A commercial installation will include typical process expedients such as recycle streams, for efficient use of reactants and reaction products, and may be integrated with process units for production of dimethyl ether or for production of products from formaldehyde.

As compared with data in patents mentioned above, the process of this invention exhibits both improved conversions of dimethyl ether as well as improved selectivity to formaldehyde, and can achieve these results at lower temperatures. The process of this invention may be operated in general at temperatures of from about 150 to about 400° C., preferably from about 180 to about 350° C., most preferably from about 150 to about 320° C. Operating pressures are about 0.1–100 atm, preferably about 1–20 atm. Residence time generally ranges from about 1 to about 60 seconds.

EXAMPLES

The following are representative examples of this invention. These examples are provided by way of illustration only and not by way of limitation. Those of skill will readily recognize a variety of noncritical parameters that could be changed or modified to yield essentially similar results.

Example 1

Production of Formaldehyde from Dimethyl Ether Using Molybdenum Catalysts Supported on Alumina, Zirconia and Stannic Oxide Supported $MoO_x$ catalysts were prepared by incipient wetness impregnation of $ZrO(OH)_2$, $SnO_2$, or $Al_2O_3$, respectively, with aqueous $(NH_4)_2Mo_2O_8$ (99%, Aldrich) solutions (13–15). $ZrO(OH)_2$ was prepared by hydrolysis of aqueous zirconyl chloride solutions (>98%, Aldrich) using $NH_4OH$ (14.8 N), followed by drying in ambient air at 393 K overnight. $SnO_2$ was prepared by hydrolysis of tin (IV) chloride pentahydrate (98%, Alfa Aesar) with $NH_4OH$ (14.8 N), followed by treatment in flowing dry air at 773 K for 3 h. A commercial source of $\gamma$-$Al_2O_3$ (Degussa AG) was used without further treatment. All samples were dried after impregnation at 373 K in ambient air and then treated in flowing dry air at 773 K for 3 h. Bulk $MoO_3$ powders were prepared by decomposition of $(NH_4)_2Mo_2O_8$ (99%, Aldrich) in flowing dry air at 773 K for 3 h.

Dimethyl ether reactions were carried out in a fixed-bed quartz microreactor using catalysts (0.3 g) diluted with quartz powder (1 g) in order to prevent local high temperatures caused by the exothermic nature of the reaction. The reactant mixture consisted of 80 kPa DME and 18 kPa $O_2$, and 2 kPa $N_2$ was used as an internal standard. Reactants and products were analyzed by on-line gas chromatography (Hewlett-Packard 6890 GC) using flame ionization and thermal conductivity detectors and methyl-silicone capillary and Porapak® Q packed columns.

Table 1 shows catalytic results obtained at 513 K on $MoO_x$ domains supported on $Al_2O_3$, $ZrO_2$ and $SnO_2$ with similar Mo surface densities (6.4–7.0 Mo-atoms/nm$^2$), alone and compared with results reported in previous patents. Rates and selectivities (in all tables) were measured as a function of DME conversion, which was changed by varying the reactant residence time. DME conversion rates and formaldehyde selectivities were extrapolated to zero reactant residence time in order to obtain primary DME conversion rates and selectivities. DME conversion rates and selectivities are reported in two forms in the results shown in Table 1. One approach considers $CH_3OH$ as a DME conversion product; the other approach reports rates and selectivities on a $CH_3OH$-free basis, which seems appropriate in view of the reversible nature of DME conversion to methanol and the pathways available for the ultimate conversion of both $CH_3OH$ and DME to HCHO.

Primary reaction rates (normalized by catalyst mass) were much higher on the three catalysts of the invention than on catalysts previously reported in the patents, even at the lower temperatures used here. Rates were higher on $SnO_2$ and $ZrO_2$ supports than on $Al_2O_3$, but the primary formaldehyde selectivity ($CH_3OH$-free) was almost 100% on $MoO_x$/$Al_2O_3$. Pure supports showed very low DME conversion rates. A $MoO_3$ sample with relatively low surface area gave a low DME conversion rate (per gram), but its areal rate resembled those on $MoO_x/Al_2O_3$ and was 2–6 times lower than on $MoO_x$ supported on $ZrO_2$ and $SnO_2$. Thus, DME conversion appears to require small $MoO_x$ domains with much greater accessibility to reactants than those available in bulk $MoO_3$ samples. Formaldehyde was not detected on $MoO_3$ at 513 K, because of the low DME conversions attained. At higher temperatures (593 K), the primary HCHO selectivity was 52.9% (on a $CH_3OH$-free basis) on bulk $MoO_3$. $MoO_x/Al_2O_3$ was the most selective catalyst for DME conversion to HCHO. Its primary HCHO selectivity was 79.1% (98.1%, $CH_3OH$-free basis) and CO and $CO_2$ ($CO_x$) were not detected as primary products.

Included in these tests was a catalyst similarly prepared comprising molybdenum oxide supported on magnesium oxide. MgO was prepared by contacting MgO (>98%, Aldrich) with deionized water at 355–365 K for 4 h, followed by treatment in flowing dry air at 773 K for 8 h. As seen from Table 1, however, $MoO_x$ domains supported on MgO did not give detectable DME conversion rates, apparently as a result of the formation of mixed metal oxides, which are unable to undergo reduction-oxidation cycles required for catalytic DME conversion turnovers at these temperatures. This support thus appears unsuitable for use with the catalysts in this process.

(2.2–30.6 $Mo/nm^2$). Primary DME reaction rates increased from 2.3 to 5.7 mol/g-atom Mo-h as the Mo surface density increased from 1.6 to 7.0 $Mo/nm^2$ on $Al_2O_3$ (Table 2). These rates increased from 0.6 to 12.2 mol/g-atom Mo-h as the Mo surface density increased from 2.2 to 6.4 $Mo/nm^2$ on $ZrO_2$. On both $ZrO_2$ and $Al_2O_3$, DME conversion rates per Mo reached maximum values at surface densities of 6–7 $Mo/nm^2$. Results are reported in Table 2.

X-Ray diffraction and Raman, UV-visible, and X-ray absorption spectroscopies did not detect $MoO_3$ crystallites in samples with surface densities below 7 $Mo/nm^2$. In this Mo surface density range, most, if not all, $MoO_x$ species are accessible at surfaces and the DME conversion rates per Mo atom are equivalent to rates per exposed $MoO_x$ moiety (i.e. turnover rates). Therefore, the higher reaction rates attained with increasing surface density reflect a higher reactivity of exposed $MoO_x$ as the size and dimensionality of $MoO_x$ domains increases with increasing Mo surface density. The larger domains formed at higher $MoO_x$ surface densities (detected by measurements of their absorption edge energy in the UV-visible spectra) appear to undergo the redox cycles required for DME conversion to HCHO with greater ease than isolated monomolybdate species or smaller two-dimensional polymolybdate domains.

This interpretation is consistent with the observed decrease in the temperature required for $H_2$ reduction of

TABLE 1

DME oxidation rates and selectivities on supported $MoO_x$ catalysts at 513 K (80.0 kPa, 18 kPa $O_2$ and 2 kPa $N_2$), on bulk $MoO_3$, on pure supports, and on previously reported catalysts.

| Catalyst ($MoO_3$ wt %) | Surface area ($m^2/g$) | Mo surface density ($Mo/nm^2$) | Temperature (K) | DIMETHYL ETHER Conversion Rate[d] (mmol/$g_{cat}$-h) | DME Conversion Rate[d] (mol/g-atom Mo-h) | DME Conversion Rate[d] ($10^{-5}$ mol/$m^2$-h) | Selectivity (%)[d] | | | | | Reference |
|---|---|---|---|---|---|---|---|---|---|---|---|---|
| | | | | | | | $CH_3OH$ | HCHO | MF[a] | DMM[b] | $CO_x$[c] | |
| $MoO_3/ZrO_2$ (20.7%) | 136.3 | 6.4 | 513 | 17.6 (13.6) | 12.2 (9.4) | 12.9 | 22.6 | 53.4 (69.0) | 16.8 (21.7) | 0.3 (0.4) | 6.9 (8.9) | This study |
| $MoO_3/SnO_2$ (7.2%) | 46.5 | 6.5 | 513 | 18.4 (16.0) | 36.5 (31.7) | 39.6 | 13.1 | 67.3 (77.6) | 9.6 (11.1) | 0 (0) | 9.8 (11.3) | This study |
| $MoO_3/Al_2O_3$ (15.0%) | 90.0 | 7.0 | 513 | 5.8 (4.7) | 5.7 (4.6) | 6.6 | 19.7 | 79.9 (98.1) | 1.6 (1.9) | 0 (0) | 0 (0) | This study |
| $MoO_3/MgO$ (24.0%) | 171.2 | 5.8 | 513 | not detected | not detected | — | — | — | — | — | — | This study |
| $ZrO_2$ | 106.4 | — | 513 | not detected | — | — | — | — | — | — | — | This study |
| $SnO_2$ | 48.8 | — | 513 | 0.6 | — | 1.2 | 29.7 | 0 | 0 | 0 | 70.3 | This study |
| $Al_2O_3$ | 110 | — | 513 | 0.2 | — | 0.2 | 82.9 | 0 | 0 | 0 | 17.1 | This study |
| $MoO_3$ | 3.3 | — | 513 | 0.2 | — | 6.1 | 6.0 | 0 | 0 | 0 | 94.0 | This study |
| [e]Ag | — | — | 887 | 10.5 | — | — | — | 45.8 | 0 | 0 | 30.7 | 10 |
| [f]Bi—Mo—$FeO_x$ | — | — | 773 | 3.1 | — | — | 0 | 46.0 | 0 | 0 | 54.0 | 7 |
| [g]Bi—Mo—$CuO_x$ | — | — | 773 | 2.9 | — | — | 0 | 43.0 | 0 | 0 | 55.0 | 8 |
| [h]Mn nodules | ~230 | — | 623 | 1.7 | — | 0.7 | — | 49.0 | — | — | — | 9 |

[a]MF: Methyl formate;
[b]DMM: dimethoxymethane;
[c]$CO_x$: CO + $CO_2$;
[d]The data in parentheses are reported on a $CH_3OH$-free basis by excluding $CH_3OH$ as a reaction product in view of its reactivity in formaldehyde synthesis and its tendency to dehydrate to re-form $CH_3OCH_3$.
[e]from U.S. Pat. No. 6,265,528; Reactants: 59.9 kPa DME, 8.5 kPa $O_2$, 31.6 kPa $N_2$.
[f]from U.S. Pat. No. 4,442,307; Reactants: 5.0 kPa DME, 20.0 kPa $O_2$, 75.0 kPa $N_2$.
[g]from U.S. Pat. No. 4,439,624; reactants same as (f);
[h]from U.S. Pat. No. 4,435,602; reactants same as (f).

Example 2
Additional Tests with Molybdenum Oxide Catalysts Supported on Alumina

A parallel study showed that the catalytic properties of these $MoO_x$ domains depend sensitively on their size and local structure, which were varied by changing the Mo surface density on $Al_2O_3$ (1.6–11.3 $Mo/nm^2$) and $ZrO_2$ $Mo^{6+}$ to $Mo^{4+}$ in these samples. Ultimately, DME conversion rates (per Mo) decreased at even higher Mo surface densities (>10 $Mo/nm^2$), because the incipient formation of three-dimensional $MoO_3$ clusters leads to increasingly inaccessible $MoO_x$ species.

Primary formaldehyde selectivities also increased monotonically with increasing Mo surface density; they reached 79.1% (98.1% on a $CH_3OH$-free basis) on $MoO_x/Al_2O_3$ at 11.3 $Mo/nm^2$. Methanol selectivities decreased as the $Al_2O_3$ support was covered with $MoO_x$ species, and the primary formaldehyde selectivity concurrently increased with increasing Mo surface density. Methyl formate and $CO_x$ primary selectivities were very low on all $Al_2O_3$-supported $MoO_x$ samples. On $Al_2O_3$-supported samples with surface densities of 1.6 to 11.3 $Mo/nm^2$, the $CH_3OH$-free primary HCHO selectivity was 95.2–98.1% (Table 2).

Example 4

Further Experiments with Molybdenum Oxide Catalysts Supported on Zirconia

A series of molybdenum oxide catalysts supported on zirconia, having a range of surface densities and prepared by

TABLE 2

Effects of surface density of $MoO_x/Al_2O_3$ catalysts on primary DME reaction rates and primary products at 513K (80.0 kPa, 18 kPa $O_2$ and kPa $N_2$).

| $MoO_3$ loading | Mo surface density | Rate$^d$ | Rate$^d$ | Selectivity (%)$^d$ | | | | |
|---|---|---|---|---|---|---|---|---|
| ($MoO_3$ wt %) | ($Mo/nm^2$) | (mol/g-atom Mo-h) | ($10^{-5}$ $mol/m^2$-h) | $CH_3OH$ | HCHO | MF$^a$ | DMM$^b$ | $CO_x$$^c$ |
| 4.0% | 1.6 | 2.3 | 0.6 | 34.1 | 62.8 | 2.5 | 0 | 0.8 |
| | | (1.5)$^d$ | (0.4)$^d$ | | (95.2) | (3.7) | (0) | (1.2) |
| 8.0% | 3.4 | 3.9 | 2.2 | 27.0 | 70.5 | 2.4 | 0 | 0.2 |
| | | (2.8) | (1.6) | | (96.5) | (3.2) | (0) | (0.3) |
| 10.0% | 4.5 | 5.2 | 4.0 | 22.1 | 76.3 | 1.5 | 0 | 0.1 |
| | | (4.1) | (3.1) | | (97.9) | (1.9) | (0) | (0.1) |
| 15.0% | 7.0 | 5.7 | 6.6 | 19.5 | 79.1 | 1.6 | 0 | 0 |
| | | (4.6) | (5.3) | | (98.1) | (1.9) | (0) | (0) |
| 20.0% | 11.3 | 3.8 | 7.1 | 19.4 | 79.0 | 1.6 | 0.1 | 0 |
| | | (3.1) | (5.7) | | (98.0) | (1.9) | (0.1) | (0) |

$^a$MF: Methyl formate;
$^b$DMM: dimethoxymethane;
$^c$$CO_x$: $CO + CO_2$;
$^d$The data in parentheses are reported on a $CH_3OH$-free basis by excluding $CH_3OH$ as a reaction product in view of its reactivity in formaldehyde synthesis and its tendency to dehydrate to re-form $CH_3OCH_3$.

Example 3
Effect of Temperature on Reaction Rates and Primary Products

Table 3 shows results of a study comparing reaction rates and selectivity at temperatures of 473–533 K (200–250° C.). The catalyst used contained 15 wt. % $MoO_3$ on alumina with a surface density of 7.0 $Mo/nm^2$. As the temperature was increased from 473 to 533 K, the reaction rate increased significantly, and selectivity to formaldehyde (as opposed to methyl formate) also increased significantly.

TABLE 3

Effects of temperature on primary DME reaction rates and primary products on $MoO_x/Al_2O_3$ catalyst (15 wt. % $MoO_3$; 7.0 $Mo/nm^2$) (80.0 kPa, 18 kPa $O_2$ and 2 kPa $N_2$).

| Temperature | Rate$^d$ (mol/g-atom Mo-h) | Selectivity (%)$^d$ | | | |
|---|---|---|---|---|---|
| | | $CH_3OH$ | HCHO | MF$^a$ | DMM$^b$ | $CO_x$$^c$ |
| 473 | 1.3 | 24.2 | 69.2 | 4.2 | 0.2 | 2.1 |
| | (1.0) | | (91.2) | (5.5) | (0.3) | (2.8) |
| 493 | 2.9 | 23.8 | 73.1 | 2.0 | 0 | 1.2 |
| | (2.2) | | (95.9) | (2.6) | (0) | (1.6) |
| 513 | 5.7 | 19.5 | 79.1 | 1.6 | 0 | 0 |
| | (4.6) | | (98.1) | (1.9) | (0) | (0) |
| 533 | 12.9 | 17.3 | 81.0 | 1.8 | 0 | 0 |
| | (10.7) | | (97.9) | (2.1) | (0) | (0) |

$^a$MF: Methyl formate;
$^b$DMM: dimethoxymethane;
$^c$$CO_x$: $CO + CO_2$;
$^d$The data in parentheses are reported on a $CH_3OH$-free basis by excluding $CH_3OH$ as a reaction product in view of its reactivity in formaldehyde synthesis and its tendency to dehydrate to re-form $CH_3OCH_3$.

calcining at two different temperatures was used to catalyze the production of formaldehyde from dimethyl ether.

The catalysts were prepared by incipient wetness impregnation of precipitated zirconium oxyhydroxide ($ZrO(OH)_2$) with an aqueous solution of ammonium dimolybdate [$(NH_4)_2Mo_2O_8$] (99%, Aldrich). Zirconium oxyhydroxide ($ZrO(OH)_2$) was prepared by precipitation of a zirconyl chloride solution (98%, Aldrich) at a constant pH of 10 by controlling the rate of addition of ammonium hydroxide solution (29.8%, Fisher Sci.). After precipitation, the solids were washed with mildly basic ammonium hydroxide solution (pH~6) until the effluent showed no chloride ions tested by a silver nitrate solution. The resulting solids were dried in air overnight at 393 K (120° C.). The dried solids were impregnated with an aqueous solution of ammonium dimolybdate at room temperature. The $Mo^{6+}$ concentrations in the solution were varied in order to get desired Mo content in the final catalysts. After impregnation, samples were dried in air at 393 K and treated in dry air at 723, 773 or 873 K (450, 500 and 600° C.) for 3 h.

The catalysts were systematically characterized by means of powder X-ray diffraction (XRD), diffuse reflectance UV-visible, Raman, and X-ray absorption (XANES/XAFS) spectroscopies. Surface areas were measured by N2 physisorption using standard multipoint BET method. Mo surface density is expressed as the number of Mo atoms per square nanometer BET surface area ($Mo/nm^2$). The catalysts so prepared are listed in Table 4.

TABLE 4

Surface areas and Mo surface density for $MoO_x/ZrO_2$ catalysts treated at 723, 773 and 873 K.

| | | 723K | | 773 K | | 873 K | |
|---|---|---|---|---|---|---|---|
| Sample | $MoO_3$ Loading (wt. %) | Surface area ($m^2/g$) | Mo surface density ($Mo/nm^2$) | Surface area ($m^2/g$) | Mo surface density ($Mo/nm^2$) | Surface area ($m^2/g$) | Mo surface density ($Mo/nm^2$) |
| $1MoO_x/ZrO_2$ | 1.0% | 118.8 | 0.3 | 105.6 | 0.4 | 85.6 | 0.5 |
| $6MoO_x/ZrO_2$ | 5.7% | 130.0 | 1.8 | 110.3 | 2.2 | 97.1 | 2.5 |
| $11MoO_x/ZrO_2$ | 11.0% | 145.9 | 3.2 | 132.6 | 3.5 | 103.4 | 4.5 |
| $21MoO_x/ZrO_2$ | 20.7% | 153.7 | 5.6 | 136.3 | 6.4 | 102.7 | 8.4 |
| $29MoO_x/ZrO_2$ | 29.3% | 114.0 | 10.7 | 96.9 | 12.6 | 64.6 | 20.0 |
| $37MoO_x/ZrO_2$ | 37.0% | 99.6 | 15.5 | 73.9 | 20.9 | 49.3 | 31.4 |
| $44MoO_x/ZrO_2$ | 44% | 83.5 | 22.0 | 60.2 | 30.6 | 36.7 | 50.1 |

Tables 5 and 6 show the results using catalysts so prepared and calcined at 773 K and 873 K, respectively. Both catalysts demonstrated very good dimethyl ether conversion rates and selectivity, with better performance being exhibited in general by the catalyst that had been calcined at 873 K.

In other work, the effect of partial pressures on the reaction was investigated on the $44MoO_x/ZrO_2$ catalyst (50.1 $Mo/nm^2$). The reaction rates nearly increased linearly as the DME partial pressure increased from 10 to 40 kPa, and then approached the constant values above 60 kPa. The primary selectivities to methyl formate and

TABLE 5

Effects of surface density of $MoO_x/ZrO_2$ catalysts (calcined at 773 K) on primary DME reaction rates and primary products at 513K (80.0 kPa, 18 kPa $O_2$, and 2 kPa $N_2$).

| $MoO_3$ loading | Mo surface density | Rate[d] | Rate[d] | Selectivity (%)[d] | | | | |
|---|---|---|---|---|---|---|---|---|
| ($MoO_3$ wt. %) | ($Mo/nm^2$) | (mol/g-atom Mo-h) | ($10^{-5}$ $mol/m^2$-h) | $CH_3OH$ | HCHO | MF[a] | DMM[b] | $CO_x$[c] |
| 11.0% | 3.5 | 8.5 | 4.9 | 24.0 | 32.3 | 30.0 | 0 | 13.7 |
| | | (6.5) | (3.7) | | (42.5) | (39.5) | (0) | (18.1) |
| 20.7% | 6.4 | 12.2 | 12.9 | 22.6 | 53.4 | 16.8 | 0.3 | 6.9 |
| | | (9.4) | (10.0) | | (68.9) | (21.7) | (0.4) | (8.9) |
| 29.3% | 12.6 | 4.1 | 8.6 | 22.3 | 62.9 | 8.4 | 0.2 | 6.4 |
| | | (3.2) | (6.7) | | (80.8) | (10.7) | (0.2) | (8.2) |
| 37.0% | 20.9 | 3.2 | 11.1 | 23.0 | 66.9 | 7.6 | 0.1 | 2.4 |
| | | (2.5) | (8.6) | | (86.9) | (9.8) | (0.1) | (3.1) |
| 44.0% | 30.6 | 2.0 | 10.4 | 22.4 | 68.6 | 5.0 | 0 | 4.0 |
| | | (1.6) | (8.1) | | (88.4) | (6.5) | (0) | (5.1) |

[a]MF: Methyl formate;
[b]DMM: dimethoxymethane;
[c]$CO_x$: CO + $CO_2$;
[d]The data in parentheses are reported on a $CH_3OH$-free basis by excluding $CH_3OH$ as a reaction product in view of its reactivity in formaldehyde synthesis and its tendency to dehydrate to re-form $CH_3OCH_3$.

TABLE 6

Effects of surface density of $MoO_x/ZrO_2$ catalysts (calcined at 873 K) on primary DME reaction rates and primary products at 513K (80.0 kPa, 18 kPa $O_2$, and 2 kPa $N_2$).

| $MoO_3$ loading | Mo surface density | Rate[d] | Rate[d] | Selectivity (%)[d] | | | | |
|---|---|---|---|---|---|---|---|---|
| ($MoO_3$ wt. %) | ($Mo/nm^2$) | (mol/g-atom Mo-h) | ($10^{-5}$ $mol/m^2$-h) | $CH_3OH$ | HCHO | MF[a] | DMM[b] | $CO_x$[c] |
| 11.0% | 4.5 | 23.0 | 17.0 | 24.9 | 46.0 | 23.5 | 0.4 | 5.2 |
| | | (17.3) | (13.0) | | (61.2) | (31.3) | (0.5) | (7.0) |
| 20.7% | 8.4 | 46.5 | 51.7 | 23.7 | 60.1 | 11.5 | 0.8 | 4.0 |
| | | (35.5) | (39.5) | | (78.6) | (15.1) | (1.1) | (5.2) |
| 29.3% | 20.0 | 19.0 | 60.0 | 24.1 | 59.6 | 12.2 | 0.9 | 3.2 |
| | | (14.4) | (45.5) | | (78.5) | (16.1) | (1.2) | (4.2) |
| 37.0% | 31.4 | 11.7 | 61.1 | 24.9 | 58.3 | 12.6 | 1.1 | 3.0 |
| | | (8.8) | (45.9) | | (77.7) | (16.8) | (1.5) | (4.0) |
| 44.0% | 50.1 | 7.4 | 61.3 | 27.8 | 60.1 | 10.4 | 0.9 | 1.3 |
| | | (5.3) | (44.3) | | (82.7) | (14.4) | (1.2) | (3.8) |

[a]MF: Methyl formate;
[b]DMM: dimethoxymethane;
[c]$CO_x$: CO + $CO_2$;
[d]The data in parentheses are reported on a $CH_3OH$-free basis by excluding $CH_3OH$ as a reaction product in view of its reactivity in formaldehyde synthesis and its tendency to dehydrate to re-form $CH_3OCH_3$.

dimethoxymethane were almost independent of the DME partial pressure. The primary selectivity to $CO_x$ decreased from 6.0% to the constant value of 1.5% while the selectivity to HCHO increased from 78.3 to 82.7% with increasing the DME pressure from 10 to 40 kPa.

Example 5
Preparation and Use of Supported Vanadium Pentoxide Catalysts

The catalysts were prepared by incipient wetness impregnation of γ-$Al_2O_3$ (Degussa AG) with an aqueous solution of ammonium metavanadate [$NH_4NO_3$] (99%, Aldrich) and oxalic acid (Mallinckrodt, analytical grade; $NH_4/NO_3$/oxalic acid=0.5 M) (the addition of oxalic acid improves the dissolution of $NH_4NO_3$ in water). The $V^{5+}$ concentrations in the solution were varied in order to get desired V content in the final catalysts. After impregnation, samples were dried in air at 393 K and treated in dry air at 773 K (500° C.) for 3 h.

On $VO_x/Al_2O_3$ (8.0 V/nm$^2$) the $CH_3OH$-free primary HCHO selectivity was 99.6% at 513 K and the primary DME reaction rate was 6.8 mol/g-atom V-h. Results are shown in Table 7.

grade) at 673 K for 3 h. $CeO_x$ and $FeO_x$-modified $Al_2O_3$ supports ($CeO_x/Al_2O_3$ and $FeO_x/Al_2O_3$) were prepared by incipient wetness impregnation of $Al_2O_3$ (Degussa AG, ~100 m$^2$/g) with aqueous solutions of $Ce(NO_3)_4$ (Aldrich, 99.99%) and $Fe(NO_3)_3$ (Aldrich, 99.9%), respectively at 289 K for 5 h, followed by drying at 393 K overnight and then treating in flowing dry air (Airgas, zero grade) at 673 K for 3 h. $SnO_2$ was prepared by hydrolysis of tin (IV) chloride pentahydrate (98%, Alfa Aesar) at a pH of ~7 using $NH_4OH$ (14.8 N, Fisher Scientific). The precipitates were washed with deionized water until the effluent was free of chloride ions. The resulting solids were treated in flowing dry air (Airgas, zero grade) at 773 K for 3 h. Supported $MoO_x$ catalysts were prepared by incipient wetness impregnation method using aqueous $(NH_4)_6Mo_7O_{24}$ (Aldrich, 99%) solutions. Supported $VO_x$ catalysts were also prepared by incipient wetness impregnation method using an aqueous solution of ammonium metavanadate [$NH_4NO_3$] (Aldrich, 99%) and oxalic acid (Mallinckrodt, analytical grade; $NH_4NO_3$/oxalic acid=0.5 M). All samples were dried at 393 K in ambient air after impregnation and then treated in flowing dry air (Airgas, zero grade) at 773 K for 3 h. The Mo or V surface density for all supported samples is reported as Mo/nm$^2$ or

TABLE 7

Primary DME reaction rates and primary products on $VO_x$ dispersed on different supports at 240° C. (80.0 kPa, 18 kPa $O_2$ and 2 kPa $N_2$).

| Catalyst | V surface density | Rate[a] | Rate[a] | Selectivity (%) | | | | |
|---|---|---|---|---|---|---|---|---|
| ($V_2O_5$ wt. %) | (V/nm$^2$) | (mol/g-atom V-h) | (10$^{-5}$ mol/m$^2$-h) | $CH_3OH$ | HCHO | MF[b] | DMM[c] | $CO_x$[d] |
| $VO_x/Al_2O_3$ (10.0%) | 8.0 | 8.0 (6.8) | 6.7 (5.6) | 14.72 | 84.96 (99.61) | 0.26 (0.3) | 0 | 0 |
| $VO_x/ZrO_2$ (15%) | 6.2 | 13.1 (12.4) | 8.5 (8.1) | 5.2 | 37.9 (40.0) | 9.2 (9.7) | 0 | 47.7 (50.3) |
| $VO_x/MgO$ (20.0%) | 5.5 | 1.8 | 1.0 | 11.0 | 0 | 0 | 0 | 89.0 |

[a]The data in the parentheses are reported on a $CH_3OH$-free basis by excluding $CH_3OH$ as a reaction product in view of its reactivity in formaldehyde synthesis and its tendency to dehydrogenate to re-from $CH_3OCH_3$;
[b]MF: methyl formate;
[c]DMM: dimethoxymethane;
[d]$CO_x$: CO + $CO_2$.

Example 6
Use of Mixed Oxide Catalysts

Similarly, experiments were conducted using a catalyst containing molybdenum oxide on a support of alumina modified by stannic oxide, cerium oxide and ferric oxide.

$SnO_x$ and $ZrO_x$-modified $Al_2O_3$ supports ($SnO_x/Al_2O_3$ and $ZrO_x/Al_2O_3$) were prepared by incipient wetness impregnation of $Al_2O_3$ (Degussa AG, ~100 m$^2$/g or ~180 m$^2$/g) with isobutanol solutions of $Sn(i-C_4H_9O)_4$ and $Zr(i-C_4H_9O)_4$ (Aldrich, 99.8%), respectively at 289 K under dry $N_2$ atmosphere for 5 h, followed by drying at 393 K overnight and then treating in flowing dry air (Airgas, zero V/nm$^2$, based on the Mo or V content and the BET surface area for each sample.

The catalysts retained the good selectivity of the molybdenum oxide/alumina catalysts but had higher activity. Results are reported in Tables 8 and 9. Table 10 shows results using vanadium oxide catalysts on alumina and on stannic oxide/alumina. As shown in Table 10, the DME conversion rates using $VO_x/SnO_x/Al_2O_3$ (5.5 Sn/nm$^2$) were about 2.4 times than the rates on $VO_x/Al_2O_3$ at 513K.

TABLE 8

Primary DME conversion rates and product selectivities for $MoO_x$ domains supported on $Al_2O_3$ modified with $SnO_x$ at different surface densities (1.5–11.2 Sn/nm$^2$) and also on unmodified $Al_2O_3$ and $SnO_2$ (~7.0 Mo/nm$^2$; 513K; 80.0 kPa DME, 18 kPa $O_2$ and 2 kPa $N_2$).

| Support | Sn surface density | [a]DME conversion rate | [a]Primary selectivity (%) | | | |
|---|---|---|---|---|---|---|
| ($MoO_3$ wt %) | (Sn/nm$^2$) | (mol/g-atom Mo-h) | HCHO | [b]MF | [c]DMM | [d]$CO_x$ |
| $Al_2O_3$ (15.0%) | 0 | 4.6 | 98.1 | 1.9 | 0 | 0 |

TABLE 8-continued

Primary DME conversion rates and product selectivities for $MoO_x$ domains supported on $Al_2O_3$ modified with $SnO_x$ at different surface densities (1.5–11.2 $Sn/nm^2$) and also on unmodified $Al_2O_3$ and $SnO_2$ (~7.0 $Mo/nm^2$; 513K; 80.0 kPa DME, 18 kPa $O_2$ and 2 kPa $N_2$).

| Support (MoO₃ wt %) | Sn surface density (Sn/nm²) | ᵃDME conversion rate (mol/g-atom Mo-h) | ᵃPrimary selectivity (%) | | | |
|---|---|---|---|---|---|---|
| | | | HCHO | ᵇMF | ᶜDMM | ᵈCOₓ |
| MoOₓ/SnO₂ (5.9%) | — | 36.4 | 70.4 | 12.5 | 0 | 17.2 |
| SnOₓ/Al₂O₃ (15.0%:) | 1.5 | 5.4 | 97.2 | 2.8 | 0 | 0 |
| SnOₓ/Al₂O₃ (15.0%) | 2.8 | 7.1 | 98.0 | 2.0 | 0 | 0 |
| SnOₓ/Al₂O₃ (15.0%) | 5.5 | 12.2 | 97.7 | 2.3 | 0 | 0 |
| SnOₓ/Al₂O₃ (13.6%) | 11.2 | 12.9 | 97.6 | 2.4 | 0 | 0 |

ᵃThe data are reported on a $CH_3OH$-free basis by excluding $CH_3OH$ as a reaction product in view of its reactivity in formaldehyde synthesis and its tendency to dehydrate to re-form $CH_3OCH_3$.
ᵇMF: Methyl formate;
ᶜDMM: dimethoxymethane;
ᵈCOₓ: $CO + CO_2$.

TABLE 9

Primary DME conversion rates and product selectivities for $MoO_x$ domains supported on unmodified $Al_2O_3$, and on $Al_2O_3$ modified with near-single monolayer $SnO_x$, $ZrO_x$, $CeO_x$, and $FeO_x$ (513K; 80.0 kPa DME, 18 kPa $O_2$, and 2 kPa $N_2$).

| Catalyst (MoO₃ wt %) | Mo surface density (Mo/nm²) | ᵃDME conversion rate (mol/g-atom Mo-h) | ᵃPrimary selectivity (%) | | | |
|---|---|---|---|---|---|---|
| | | | HCHO | ᵇMF | ᶜDMM | ᵈCOₓ |
| MoOₓ/Al₂O₃ (15.0%) | 7.0 | 4.6 | 98.1 | 1.9 | 0 | 0 |
| MoOₓ/SnOₓ/Al₂O₃ (15.0%) | 7.1 | 12.2 | 97.7 | 2.3 | 0 | 0 |
| MoOₓ/ZrOₓ/Al₂O₃ (15.0%) | 6.8 | 8.7 | 98.6 | 1.4 | 0 | 0 |
| MoOₓ/CeOₓ/Al₂O₃ (13.4%) | 6.6 | 6.8 | 98.8 | 1.2 | 0 | 0 |
| MoOₓ/FeOₓ/Al₂O₃ (14.1%) | 6.7 | 6.2 | 99.7 | 0.3 | 0 | 0 |

ᵃThe data are reported on a $CH_3OH$-free basis by excluding $CH_3OH$ as a reaction product in view of its reactivity in formaldehyde synthesis and its tendency to dehydrate to re-form $CH_3OCH_3$.
ᵇMF: Methyl formate;
ᶜDMM: dimethoxymethane;
ᵈCOₓ: $CO + CO_2$.

TABLE 10

Primary DME conversion rates and product selectivities on $VO_x$ domains at near-single monolayer V surface density supported on unmodified and $SnO_x$-modified $Al_2O_3$ (5.5 $Sn/nm^2$) (513K; 80.0 kPa DME, 18 kPa $O_2$, and 2 kPa $N_2$).

| Catalyst (MoO₃ wt %) | Mo surface density (Mo/nm²) | ᵃDME Conversion Rate (mol/g-atom Mo-h) | ᵃPrimary selectivity (%) | | | |
|---|---|---|---|---|---|---|
| | | | HCHO | ᵇMF | ᶜDMM | ᵈCOₓ |
| VOₓ/Al₂O₃ (10.0%) | 8.0 | 6.8 | 99.6 | 0.4 | | 0 |
| VOₓ/SnOₓ/Al₂O₃ (10.1%) | 7.9 | 16.3 | 97.7 | 2.3 | | 0 |

ᵃThe data are reported on a $CH_3OH$-free basis by excluding $CH_3OH$ as a reaction product in view of its reactivity in formaldehyde synthesis and its tendency to dehydrate to re-form $CH_3OCH_3$.
ᵇMF: Methyl formate;
ᶜDMM: dimethoxymethane;
ᵈCOₓ: $CO + CO_2$.

Tables 11 and 12 show the effects of BET surface area of the $MoO_x$ and $VO_x$ catalysts on the primary DME conversion rates and product selectivities at 513 K. The rates normalized by the mass of the catalysts were proportional to their surface areas, while the rates normalized by Mo or V atoms and the HCHO selectivities were essentially independent of the surface area of the catalysts.

For example, on $MoO_x/Al_2O_3(B)$, the DME conversion rate per gram catalyst increased from 4.7 mmol/g-cat-h to 9.4 mmol/g-cat-h, i.e., by a factor of two as the surface area increased from 90.0 m$^2$/g for $MoO_x/Al_2O_3(A)$ to 174.9 m$^2$/g. The rate per Mo atom (4.7 vs. 5.1 mmol/g-atom Mo-h) and the primary HCHO selectivity (98.1% vs. 96.0%) values remained essentially unchanged, reflecting no change in the catalytic properties of the active $MoO_x$ sites with changing the surface area of the samples.

of clarity of understanding, it will be readily apparent to those of ordinary skill in the art in light of the teachings of this invention that certain changes and modifications may be made thereto without departing from the spirit or scope of the appended claims.

What is claimed is:

1. A process for the production of formaldehyde by oxidation of dimethyl ether in the presence of a supported catalyst comprising molybdenum oxide, vanadium oxide or a mixture of molybdenum and vanadium oxides, wherein the support is selected from catalyst supports that allow the formation of monolayers of molybdenum and/or vanadium oxide on the surface of the support but that do not substantially react with the molybdenum and/or vanadium oxide to form unreducible mixed oxides, wherein the molybdenum oxide, vanadium oxide, or mixture of such oxides is dispersed on the surface of the support, the surface density of the oxide or oxides on the support being greater than the surface density of the respective isolated monomeric oxide or oxides, and wherein the catalyst is characterized by a substantial absence of bulk crystalline molybdenum and/or vanadium oxides.

TABLE 11

Surface area effects on primary DME conversion rates and product selectivities for $MoO_x$ domains at near one monolayer surface density supported on unmodified and $SnO_x$-modified $Al_2O_3$ (~5.5 Sn/nm$^2$) (513 K; 80.0 kPa DME, 18 kPa $O_2$, and 2 kPa $N_2$).

| Support | BET surface area (m$^2$/g-cat) | Mo surface density (Mo/nm$^2$) | [a]DME conversion rate (mmol/g-cat-h) | [a]DME conversion rate (mol/g-atom Mo-h) | [a]Primary HCHO selectivity (%) | | | |
|---|---|---|---|---|---|---|---|---|
| | | | | | HCHO | [b]MF | [c]DMM | [d]$CO_x$ |
| $Al_2O_3$ (A) (15.0%) | 90.0 | 7.0 | 4.7 | 4.6 | 98.1 | 1.9 | 0 | 0 |
| $Al_2O_3$ (B) (26.8%) | 174.7 | 6.4 | 9.4 | 5.1 | 95.9 | 3.1 | 0 | 0 |
| $SnO_2/Al_2O_3$ (A) (15.0%) | 87.9 | 7.1 | 12.6 | 12.1 | 97.7 | 2.3 | 0 | 0 |
| $SnO_2/Al_2O_3$ (B) (22.9%) | 150.3 | 6.4 | 18.4 | 11.4 | 98.2 | 1.8 | 0 | 0 |

[a]The data are reported on a $CH_3OH$-free basis by excluding $CH_3OH$ as a reaction product in view of its reactivity in formaldehyde synthesis and its tendency to dehydrate to re-form $CH_3OCH_3$.
[b]MF: Methyl formate;
[c]DMM: dimethoxymethane;
[d]$CO_x$: CO + $CO_2$.

TABLE 12

Surface area effects on primary DME conversion rates and product selectivities for $VO_x$ domains at near one monolayer surface density supported on unmodified and $SnO_x$-modified $Al_2O_3$ (~5.5 Sn/nm$^2$) (513 K; 80.0 kPa DME, 18 kPa $O_2$, and 2 kPa $N_2$).

| Support ($V_2O_5$ %) | BET surface area (m$^2$/g-cat) | V surface density (V/nm$^2$) | [a]DME conversion rate (mmol/g-cat-h) | [a]DME conversion rate (mol/g-atom V-h) | [a]Primary HCHO selectivity (%) | | | |
|---|---|---|---|---|---|---|---|---|
| | | | | | HCHO | [b]MF | [c]DMM | [d]$CO_x$ |
| $Al_2O_3$ (A) (10.0%) | 83.0 | 8.0 | 6.7 | 6.8 | 99.6 | 0.4 | 0 | 0 |
| $Al_2O_3$ (B) (23.2%) | 195.9 | 7.8 | 13.5 | 5.9 | 97.1 | 2.9 | 0 | 0 |
| $SnO_2/Al_2O_3$ (A) (10.1%) | 84.3 | 7.9 | 16.2 | 16.3 | 97.7 | 2.3 | 0 | 0 |
| $SnO_2/Al_2O_3$ (B) (16.8%) | 149.2 | 7.5 | 25.3 | 15.3 | 98.0 | 2.0 | 0 | 0 |

[a]The data are reported on a $CH_3OH$-free basis by excluding $CH_3OH$ as a reaction product in view of its reactivity in formaldehyde synthesis and its tendency to dehydrate to re-form $CH_3OCH_3$.
[b]MF: Methyl formate;
[c]DMM: dimethoxymethane;
[d]$CO_x$: CO + $CO_2$.

All publications and patent applications cited in this specification are herein incorporated by reference as if each individual publication or patent application were specifically and individually indicated to be incorporated by reference.

Although the foregoing invention has been described in some detail by way of illustration and example for purposes 2. A process according to claim 1 in which the surface density of the oxide or oxides on the support is from about 50% of the surface density of a monolayer of the oxide or oxides to about 300% of the surface density of a monolayer of the oxide or oxides.

3. A process according to claim 1 in which the surface density of the oxide or oxides on the support is approximately that of a monolayer of said oxide or oxides.

4. A process according to claim 1 in which the support is selected from alumina, zirconia, titania, silica, and mixtures thereof.

5. A process according to claim 1 in which the oxide comprises molybdenum oxide.

6. A process according to claim 5 in which the support comprises alumina.

7. A process according to claim 5 in which the support comprises zirconia.

8. A process according to claim 5 in which the support comprises one or more reducible metal oxides.

9. A process according to claim 8 in which the reducible metal oxides are selected from reducible oxides of tin, iron, cerium, manganese, cobalt, nickel, chromium, rhenium, titanium, silver and copper, and mixtures thereof.

10. A process according to claim 9 in which the reducible metal oxide is selected from oxides of tin, iron, cerium, and mixtures thereof.

11. A process according to claim 8 in which the reducible metal oxide comprises stannic oxide.

12. A process according to claim 8 in which the support comprises one or more layers of a reducible metal oxide or a mixture of such oxides disposed on a particulate alumina or zirconia.

13. A process according to claim 12 in which the support comprises a layer of stannic oxide disposed on a particulate alumina or zirconia.

14. A process according to claim 5 in which the surface density of the molybdenum oxide is from about 1.5 to about 20 Mo/nm$^2$.

15. A process according to claim 6 in which the surface density of the molybdenum oxide is from about 50% of the surface density of a molybdenum oxide monolayer on the alumina support to about 300% of the surface density of a molybdenum oxide monolayer on the support.

16. A process according to claim 7 in which the surface density of the molybdenum oxide is from about 1.5 to about 50 Mo/nm$^2$.

17. A process according to claim 7 in which the surface density of the molybdenum oxide is from about 50% of the surface density of a molybdenum oxide monolayer on the zirconia support to about 400% of the surface density of a molybdenum oxide monolayer on the support.

18. A process according to claim 5 in which the surface density of the molybdenum oxide is approximately that of a monolayer of molybdenum oxide on the support.

19. A process according to claim 1 in which the oxide is vanadium oxide.

20. A process according to claim 19 in which the support comprises alumina.

21. A process according to claim 19 in which the support comprises zirconia.

22. A process according to claim 19 in which the support comprises one or more reducible metal oxides.

23. A process according to claim 22 in which the reducible metal oxides are selected from reducible oxides of tin, iron, cerium, manganese, cobalt, nickel, chromium, rhenium, titanium, silver and copper, and mixtures thereof.

24. A process according to claim 23 in which the reducible metal oxide is selected from oxides of tin, iron, cerium, and mixtures thereof.

25. A process according to claim 22 in which the reducible metal oxide comprises stannic oxide.

26. A process according to claim 22 in which the support comprises one or more layers of a reducible metal oxide or a mixture of such oxides disposed on a particulate alumina or zirconia.

27. A process according to claim 26 in which the support comprises a layer of stannic oxide disposed on particulate alumina or zirconia.

28. A process according to claim 19 in which the surface density of the vanadium oxide on the support is from about 50% of the surface density of a monolayer of vanadium oxide to about 300% of the surface density of a monolayer of vanadium oxide.

29. A process according to claim 1 in which methyl formate is a co-product with the formaldehyde.

30. A process according to claim 1 in which selectivity to formaldehyde is 50% or greater.

31. A process for the production of formaldehyde by oxidation of dimethyl ether in the presence of a supported catalyst comprising molybdenum oxide, vanadium oxide or a mixture of molybdenum and vanadium oxides, wherein the support is selected from alumina, zirconia, titania and silica, and mixtures thereof, wherein the surface density of the oxide or oxides on the support is from about 50% of the surface density of a monolayer of the oxide or oxides to about 300% of the surface density of a monolayer of the oxide or oxides, and wherein the catalyst is characterized by a substantial absence of bulk crystalline molybdenum and/or vanadium oxides.

32. A process according to claim 31 in which the surface density of the molybdenum or vanadium oxide or mixture of said oxides on the support is approximately that of a monolayer of said oxide or oxides on the support.

33. A process according to claim 31 in which the oxide is molybdenum oxide.

34. A process according to claim 33 in which the support comprises alumina.

35. A process according to claim 33 in which the support comprises zirconia.

36. A process according to claim 33 in which the catalyst comprises a layer of zirconia disposed on particulate alumina.

37. A process according to claim 31 in which the support comprises one or more reducible metal oxides.

38. A process according to claim 37 in which the reducible metal oxides are selected from reducible oxides of tin, iron, cerium, manganese, cobalt, nickel, chromium, rhenium, titanium, silver and copper, and mixtures thereof.

39. A process according to claim 37 in which the reducible metal oxide is selected from oxides of tin, iron, cerium, and mixtures thereof.

40. A process according to claim 37 in which the reducible metal oxide comprises stannic oxide.

41. A process according to claim 37 in which the support comprises one or more layers of a reducible metal oxide or a mixture of such oxides disposed on a particulate alumina or zirconia.

42. A process according to claim 37 in which the support comprises a layer of stannic oxide disposed on a particulate alumina or zirconia.

43. A process according to claim 33 in which the surface density of the molybdenum oxide is from about 1.5 to about 20 Mo/nm$^2$.

44. A process according to claim 33 in which the surface density of the molybdenum oxide is from about 50% of the surface density of a molybdenum oxide monolayer to about 300% of the surface density of a molybdenum oxide monolayer.

45. A process according to claim 33 in which the surface density of the molybdenum oxide is from about 1.5 to about 50 Mo/nm$^2$.

46. A process according to claim 33 in which the surface density of the molybdenum oxide is from about 50% of the surface density of a molybdenum oxide monolayer to about 400% of the surface density of a molybdenum oxide monolayer.

47. A process according to claim 33 in which the surface density of the molybdenum oxide is approximately that of a monolayer of molybdenum oxide.

48. A process according to claim 31 in which the oxide is vanadium oxide.

49. A process according to claim 48 in which the support comprises alumina.

50. A process according to claim 48 in which the support comprises zirconia.

51. A process according to claim 48 in which the support comprises one or more reducible metal oxides.

52. A process according to claim 51 in which the reducible metal oxides are selected from reducible oxides of tin, iron, cerium, manganese, cobalt, nickel, chromium, rhenium, titanium, silver and copper, and mixtures thereof.

53. A process according to claim 51 in which the reducible metal oxide is selected from oxides of tin, iron, cerium, and mixtures thereof.

54. A process according to claim 51 in which the reducible metal oxide comprises stannic oxide.

55. A process according to claim 51 in which the support comprises one or more layers of a reducible metal oxide or a mixture of such oxides disposed on a particulate alumina or zirconia.

56. A process according to claim 55 in which the support comprises a layer of stannic oxide disposed on a particulate alumina or zirconia.

57. A process according to claim 48 in which the surface density of the vanadium oxide on the support is from about 50% of the surface density of a monolayer of vanadium oxide to about 300% of the surface density of a monolayer of vanadium oxide.

58. A process according to claim 31 in which methyl formate is a co-product with the formaldehyde.

59. A process according to claim 31 in which selectivity to formaldehyde is 50% or greater.

60. A process for the oxidation of methanol to formaldehyde comprising contacting the methanol with a catalyst comprising molybdenum oxide vanadium oxide, or a mixture of molybdenum oxide and vanadium oxide supported on a support comprising one or more layers comprised of a reducible metal oxide or a mixture of reducible metal oxides; the reducible oxide layer or layers being disposed on a particulate alumina or zirconia support, wherein the surface density of the molybdenum and/or vanadium oxide or oxides on the support is greater than that for the respective monomeric isolated oxide or oxides, and the catalyst is characterized by a substantial absence of bulk crystalline molybdenum and/or vanadium oxides.

61. A process for the oxidative dehydrogenation of an alkane comprising contacting the alkane with a catalyst comprising molybdenum oxide, vanadium oxide, or a mixture of molybdenum oxide and vanadium oxide supported on a support comprising one or more layers comprised of a reducible metal oxide or a mixture of reducible metal oxides; the reducible oxide layer or layers being disposed on a particulate alumina or zirconia support, wherein the surface density of the molybdenum and/or vanadium oxide or oxides on the support is greater than that for the respective monomeric isolated oxide or oxides, and the catalyst is characterized by a substantial absence of bulk crystalline molybdenum and/or vanadium oxides.

62. A process for the oxidation of an alkene comprising contacting the alkene with a catalyst comprising molybdenum oxide, vanadium oxide, or a mixture of molybdenum oxide and vanadium oxide supported on a support comprising one or more layers comprised of a reducible metal oxide or a mixture of reducible metal oxides; the reducible oxide layer or layers being disposed on a particulate alumina or zirconia support, wherein the surface density of the molybdenum and/or vanadium oxide or oxides on the support is greater than that for the respective monomeric isolated oxide or oxides, and the catalyst is characterized by a substantial absence of bulk crystalline molybdenum and/or vanadium oxides.

* * * * *